United States Patent [19]
Murphy

[11] 3,990,435
[45] Nov. 9, 1976

[54] BREATH SOUND DIAGNOSTIC APPARATUS

[76] Inventor: Raymond L. H. Murphy, 38 Cyprus Road, Wellesley, Mass. 02181

[22] Filed: Sept. 30, 1974

[21] Appl. No.: 510,286

[52] U.S. Cl. ............................ 128/2 K; 128/2.05 S; 346/33 ME
[51] Int. Cl.² .......................................... A61B 7/00
[58] Field of Search ...................... 128/2 K, 2.05 S; 346/33 ME

[56] References Cited
UNITED STATES PATENTS

| | | | |
|---|---|---|---|
| 2,073,412 | 3/1937 | Cappelli | 128/2 K X |
| 2,647,033 | 7/1953 | Faus | 346/136 X |
| 2,949,910 | 8/1960 | Brown et al. | 128/2.05 S |
| 3,140,710 | 7/1969 | Glassner et al. | 128/2.05 S |
| 3,145,578 | 8/1964 | Kampf | 346/136 UX |
| 3,181,528 | 5/1965 | Brackin | 128/2 K |
| 3,188,645 | 6/1965 | Trumpy et al. | 346/33 ME |
| 3,221,334 | 11/1965 | Jones, Jr. | 346/33 MAG X |
| 3,683,398 | 8/1972 | Worley | 346/33 ME X |

Primary Examiner—Kyle L. Howell
Attorney, Agent, or Firm—Cesari & McKenna

[57] ABSTRACT

An apparatus for detecting breathing abnormalities forms a visual display of the breath sounds of a patient using a time-expanded scale on the order of meters per second to thereby delineate the differentiating sonic characteristics of these sounds. Breathing abnormalities such as coarse and fine rales, which are normally difficult to distinguish from each other, as well as abnormalities such as rhonchi are readily perceived and distinguished, and early diagnosis of diseases such as bronchities and bronchial pneumonia may thereby be facilitated.

6 Claims, 12 Drawing Figures

BREATH SOUND DIAGNOSTIC APPARATUS

BACKGROUND OF THE INVENTION

1. Field of the Invention

The invention relates to a diagnostic apparatus and, more particularly to an apparatus for detecting breathing abnormalties in humans.

2. Prior Art

Breath sounds generated by humans are of two primary types, namely, tracheal (also referred to as bronchial) breath sounds which are generated by the passage of air through the major airways between the mouth and the lungs, and vesicular breath sounds which are normally detected over most of the chest of a human. These sounds have heretofore generally been observed by placing a stethoscope over the major airways in the case of broncheal sounds or other areas of the chest in the case of vesicular sounds and listening to the sounds directly. More recently, the observations have been assisted by the use of an electronic stethoscope which amplifies the breath sounds.

Abnormal breath sounds can frequently provide significant information about pulmonary and associated abnormalities which are not readily detected by other means such as roentgenographic examination. The major types of abnormal breath sounds have been described by various observers. A useful and commonly used classification divides abnormal (or adventitious, that is, unexpected) breath sounds into two major types, namely, pulmonary and pleural. The pulmonary sounds are divided into rales, which are discontinuous (interrupted) sounds, and rhonchi, which are continuous (uninterrupted) sounds. These are further subdivided into coarse, medium and fine rales, and sibilant and sonorous rhonchi. The pleural sounds are divided into friction rub sounds and various sounds of the left pneumothorax or pneumomediastinum.

Heretofore it has been difficult for an observer to detect the various breathing abnormalities, since they are frequently of short duration, sometimes of relatively low amplitude, and generally mixed in with normal breathing sounds which sometimes obscures the abnormal sounds. Further, some of these abnormalities are difficult to distinguish from each other. When the breath sounds are monitored aurally only, the differing characteristics and observational abilities of the observer tends to play a disproportionately large role in the diagnosis because of the difficulty in aurally indentifying and classifying the sounds, and thus the diagnostic conclusions drawns from these examinations are frequently highly variable. Recordings of these sounds at conventional strip-chart recordings speeds (25–50 mm/sec) provide little additional assistance in the analysis. These factors have greatly contributed to the lack of widespread utilization of abnormal breath sounds as a useful diagnostic tool Attempts have been made to remedy this problem by mathematically analyzing the various breath sounds. This has been done by recording the sounds on a recording medium such as a magnetic tape, paper tape, or other permanent record medium and feeding the recorded data to a data processor for various analyses. For example, various studies have been directly toward analyzing the spectral frequency of the sounds, their relative amplitudes, correlation characteristics, etc. These highly sophisticated techniques have provided some generalized information about the various breath abnormalities, but have not heretofore yielded any practical, clearly defined, consistently repeatable method of distinguishing the various abnormalities or insuring their detection. Further, they are time consuming and expensive and require access to substantial equipment not commonly available outside research facilities; thus, they are not readily suited for widespread clinical use.

BRIEF DESCRIPTION OF THE INVENTION

1. Objects of the Invention

Accordingly, it is an object of the invention to provide an improved apparatus for detecting breathing abnormalities.

Further, it is an object of the invention to provide an improved apparatus for detecting and differentiating rales and rhonchi.

A further object of the invention is to provide a simple apparatus for observing breathing abnormalities which is especially useful in a clinical environment.

2. Summary of the Invention

I have found that breathing abnormalities such as rales and rhonchi are readily detected and classified by forming a visual record of the breath sound on a timeexpanded scale. In particular, I have found that when a visual record of a breath sound is made at a recording speed in excess of 400 mm/sec and, preferably, in excess of 800 mm/sec the various breathing abnormalities such as rales and rhonchi are readily detected, and, indeed, easily differentiated.

Typically, I utilize a two second breath sample for the recording. This constitutes only approximately 50% of the typical breath duration of from 3 to 5 seconds, yet, in most cases, provides all the information necessary to detect breathing abnormalities.

The recording speeds I use are considerably in excess of speeds obtainable with the more commonly available recorders utilized to record medical data (e.g., standard electrocardiographs which typically operate at recording speeds of the order of 25 mm/sec). According, I "expand" the effective time base of the breath sounds prior to recording, so that the record is formed at an effective recording rate far in excess of the actual recording rate. I accomplish this by first digitizing the breath sounds as they are received from a stethoscope pick-up, temporarily storing the digitized information, and then reading it out to a visual display medium at a lower rate corresponding to the desired display rate. Effectively, this "expands" the time base axis of the breath sound data. With this technique, rales can readily be distinguished from rhonchi; further, fine and coarse rales can be more readily distinguished from each other, as well as from medium rales.

The rales first begin to appear distinguishable at a recording rate of approximately 400 mm/sec. With respect to standard strip-chart recorders which operate at a speed of approximately 25 mm/sec, it constitutes an expansion of the time base by a factor of 16. At an effective recording speed of 800 mm/sec (corresponding to a time base expansion by a factor of 20 with respect to standard strip-chart recorders) good detail and definition appear in the recording and the results are quite useful to the practitioner in a clinical environment such as in a hospital or a physician's office. For purposes of research, however, I prefer to operate at a recording speed approximately twice this amount, that is, at a speed of 1670 mm/sec. At this speed the details of even the "fastest" transient associated with the breath sounds are readily observable. This rate is about 40 times that of the conventional medical strip-chart recorder.

The apparatus which implements the method is quite simple in design and construction, relatively inexpensive, and easily operable by medical personnel after only the briefest training. Accordingly, it is especially well suited to clinical use by the physician, that is, use in a hospital or in a doctor's office. Further, the results are readily interpreted by medical personnel, since the breath sound tracings formed by the method are directly correlated with the large body of diagnostic information based on manual chest auscultation to which the physician has already been exposed in his training. Thus, the "learning time" in connection with the method is minimal. This is to be contrasted with other techniques such as frequency spectral analysis, correlation techniques, etc. which require substantial mathematical background for a full understanding of the output data.

DETAILED DESCRIPTION OF THE INVENTION

Figure 1:
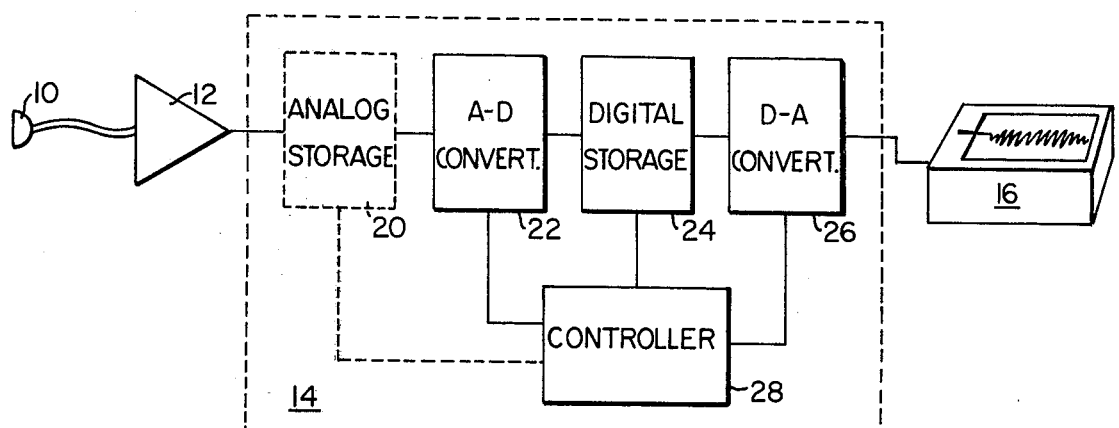
Figure 2A:
Figure 2B:
Figure 2C:
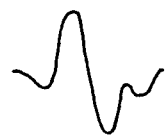
Figure 2D:
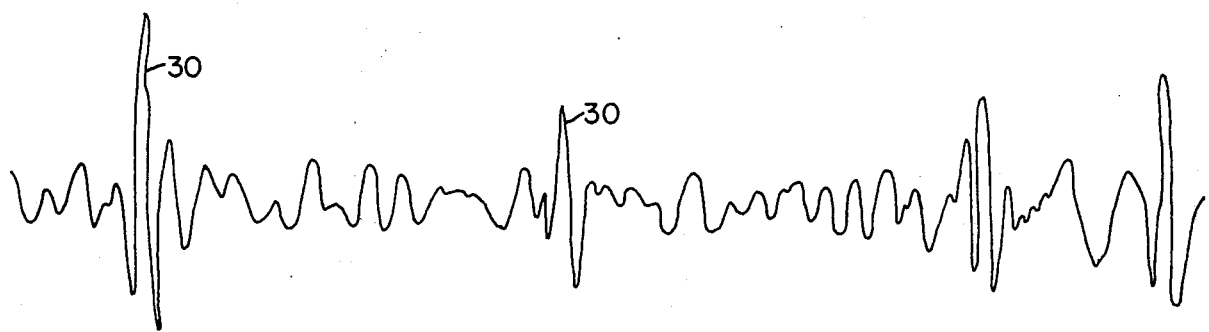
Figure 3A:
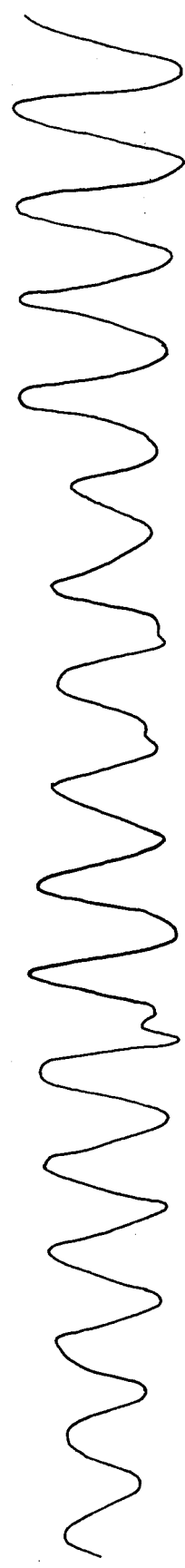
Figure 3B:
Figure 3C:
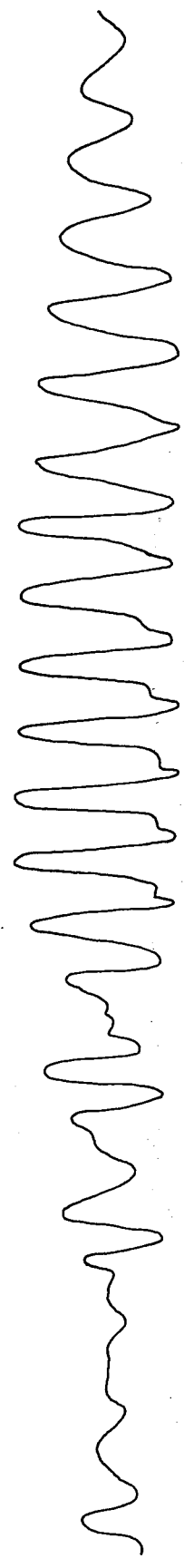
Figure 4A:
Figure 4B:
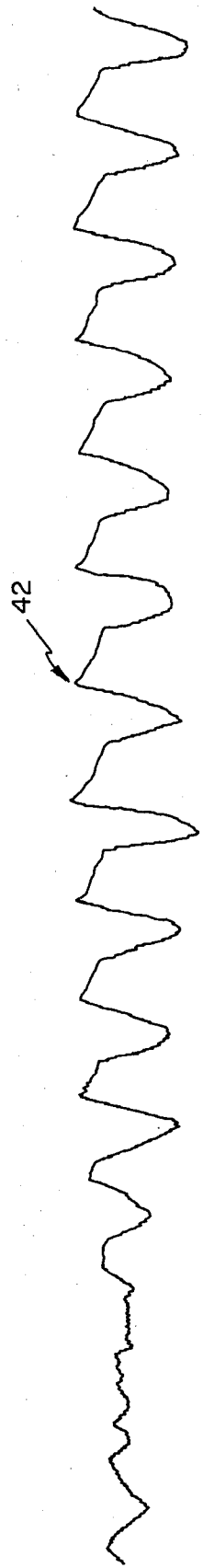
Figure 4C:
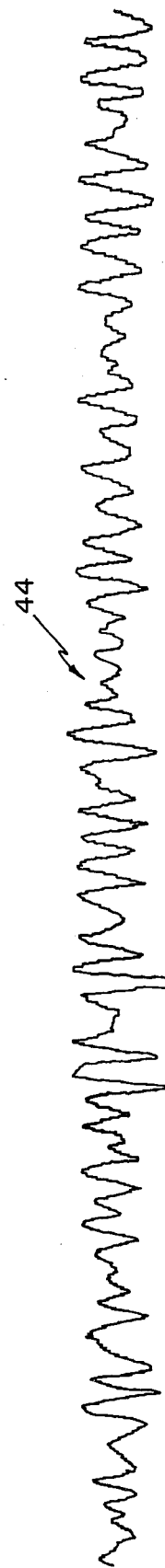
Figure 4D:

The foregoing and other and further objects and features of the invention will be more readily understood from the following detailed description of the invention when taken in connection with the accompanying drawings in which:

FIG. 1 is a block and line diagram of a breath sound recorder in accordance with the present invention;

FIGS. 2A–C are illustrations of fine, medium and coarse rales, respectively, and FIG. 2D is an illustrative tracing of a series of fine rales as seen on a time-expanded recording;

FIGS. 3A–3C are illustrative tracings of sonerous rhonchi, sibilant rhonchi and pleural friction rub waveforms, respectively, as recorded in a time-expanded recording in accordance with the invention, and FIGS. 4A–4D are illustrative waveforms showing fine rales, sonorous rhonchi, sibilant rhonchi, and normal breath waveforms, respectively.

In FIG. 1, an electronic stethoscope 10, which is examined, is connected through amplifier 12 to a time-base translator 14 whose output is displayed on a display 16.

The stethoscope 10 has a frequency response when it is essentially flat over a frequency range of from 50 to 1500 Hz; this encompasses the frequency range of the breath sounds of interest while filtering out extraneous noises beyond their frequency range. The amplifier 12 comprises a conventional analog amplifier which accepts the typically low-level (e.g. milivolt) output of the stethoscope 10 and amplifies it to a level sufficient to drive the translator 14. Preferably the gain of the amplifier 12 is adjustable to accomodate the differing transmission characteristics of various patients. The recorder 16 provides a permanent visual record and advantageously comprises a "strip-chart" recorder in which a stylus moves laterally over a chart which is driven longitudinally past the stylus.

The translator 14 accomodates the data rate at the output of the stethoscope 10 to the recording characteristics of the recorder 16 to enable the formation of a record of the breath sounds with the desired time-expanded scale. If the recorder 16 were itself able to form permanent or at least semi-permanent records of substantial length (thousands of milimeters) in a short time span (2 seconds), the translator 14 would be unnecessary. However, most commonly available recorders (other than special laboratory recorders such as transient recorders) do not have this capability, and thus the translator 14 is necessary to accomodate the incoming data rate to the desired recording rate. To this end, the translator includes an input analog storage unit 20, an analog to digital converter 22, a digital storage unit 24, a digital to analog converter 26, and a controller 28. The analog storage unit 20 receives the analog output of the stethoscope 10 and stores it for subsequent processing. It may also provide rate conversion (such as by recording at one speed and playback at another), but this will not be generally necessary. Typically, the storage unit 20 comprises an analog tape recorder which is connectable from the remainder of the translator. This facilitates data gathering at a site remote from the remainder of the translator and the output recorder, and enables the use of a single, centrally located translator and output recorder with a number of portable data-gathering input recorders. The storage unit 20 may, of course, be dispensed with and the output of the stethoscope applied directly to the converter 22 by the amplifier 12.

The analog to digital converter 22 digitizes the analog data presented to it. In one embodiment I have utilized, the converter samples the analog data and digitizes it into tenbit words at a rate of 4,000 words per second. This is more than adequate to provide accurate sampling of the breath sounds, since the frequency content of the diagnostically important sounds rarely exceeds 1,000 Hz on the basis of observations to date. The digital storage unit or "memory" 24 receives the output of converter 22 and stores it for subsequent use by the converter 26. The memory 24 may take any of numerous forms, but advantageously comprises an electronic memory such as a magnetic core or a semiconductor memory which stores the input data in a number of addressable registers for subsequent retrieval.

The converter 26 reconverts the digital data to a reconstituted analog form. In doing so, however, it operates under the control of a controller 28 which effectuates the time-base change necessary to accomodate the data rate from the stethoscope to the recording characteristics of the particular recorder 16 being utilized. In the present case, the controller 28 accomplishes this by causing the read-out of data from the storage 24 to the converter 26 at a rate different from the rate at which it was read in. For example, assume that it is desired to display a two-second sample of breath sounds on a time scale which would correspond to a recording rate of 1600 mm/sec (milimeters per second) and that the maximum recording rate of recorder 16 is 40 mm/sec. If data is received from the stethoscope 10 and sampled by the converter 22 at the rate of 4,000 words per second, the desired speed translation can be accomplished by reading the data out from memory at the rate of 100 words per second and applying it to the recorder 16. Read-out of the original two second sample would then occupy 80 seconds and, effectively, the time scale will have been expanded by a factor of 40 to one.

As seen in FIG. 1, controller 28 is connected to the converter 22, the storage unit 24, and to the converter 26; it may also be connected to the analog storage unit 20 to cause read-out at a desired time. In addition to supplying the master timing signal for the analog to digital converter 22, it also sets the rate at which the digital to analog converter 26 reads out the data from storage 24. Preferably, it is adjustable to allow variation of the data conversion rates so as to thereby accomodate different recorder devices and different desired recording rates. The controller may, of course, be incorporated directly into the respective converters 22, 26.

Samples of various types of rales and rhonchi as recorded on a time-expanded scale in accordance with the present invention are shown in FIGS. 2 through 4. The recordings were at an effective recording rate of 1670 cm/sec. FIGS. 2A through 2C show fine, medium and coarse rales, respectively. The fine rales have a characteristic somewhat resembling a damped sinusoid with a primary frequency component of approximately 700 Hz; the medium and coarse rales have an oscillatory shape, with primary frequency components of 400 Hz and 250 Hz, respectively. FIG. 2D shows a group of fine rales in a breath segment recording that is approximately 16 ms in duration. The structure of these rales shows up quite clearly and their contrast with the accompanying background sounds is marked.

Sonorous and sibilant rhonchi are shown in FIGS. 3A and B, respectively. It can be seen from these figures that the rhonchi are generally continuous sounds, and are reasonably regular and periodic; this is to be contrasted with rales which are intermittent (discontinuous). The sibilant rhonchi have an appearance that are quite similar to that of the sonorous rhonchi but differ in frequency, the sibilant rhonchi having a primary frequency component on the order of 300–400 Hz and the sonorous rhonchi having a primary frequency component on the order of approximately 200 Hz. These rhonchi may be compared with the sound of a pleural friction rub which is shown in FIG. 3C. This obviously is quite similar to the rhonchi but has a somewhat greater number of discontinuities. Frequently it is quite difficult to differentiate the rhonchi from the pleural friction rub, but the present technique readily assists one in doing so.

FIG. 4 is a "strip-chart" type recording made at an effective recording rate of 1670 mm/sec. The waveform labelled 40, shows several fine rales superimposed on a background of otherwise normal breathing sounds. The waveform labelled 42 shows a clear example of a sonorous rhonchus; this should be contrasted with the higher frequency sibilant rhonchus shown in the waveform labelled 44. Finally, a recording of the normal breath sounds is shown in the waveform labelled 46. A comparison of these traces will show the ease with which various breathing abnormalities, especially those characterized as fine rales, are detected in accordance with the present invention.

From the foregoing, it will be seen that I have provided a method and apparatus for detecting and classifying breathing abnormalities. The method is non-invasive, atraumatic, simple to use, and the results readily classified with high repeatability. The necessary recordings may readily be made by relatively untrained personnel, and can be interpreted by them after a minimum of training. Thus, the technique is well adapted to in-hospital use.

The apparatus to carry out the necessary data-rate conversion is simple in design, construction and operation and requires a minimum of training to operate. Further, it is especially adapted to centralized location of the main conversion components, so that the data collection may be performed in numerous remote locations by means of a separately detachable stethoscope, amplifier and analog signal tape recorder, and the recorded information then brought to the location of the converter for processing and re-recording at the desired recording rate.

It will be clear from the foregoing that numerous modifications may be made in the invention without departing from either the spirit or the scope thereof and, accordingly, it is intended that the foregoing be taken as illustrative only and not in a limiting sense; the scope of the invention being defined with more particularity in the following claims:

I claim:
1. A breath sound analyzer for detecting breathing abnormalities in a human, comprising:
   A. a recorder forming a visible record of data applied thereto;
   B. a data translator connected to supply data for recording to said recorder and including means for expanding the effective time base of data applied as input to said recorder, said means comprising,
      1. an analog to digital converter for converting data presented as input thereto into digital form;
      2. means for storing the digitized data;
      3. a digital to analog converter connected to said storage means for converting data stored therein to analog form; and
      4. means interconnecting said analog to digital converter and said recorder for supplying data to said recorder from said converter at a substantially lower rate than the rate at which data is supplied to the analog to digital converter; and
   c. a transducer for monitoring the breath sounds in said human and connected to apply as input to said translator signals indicative of the breath sounds.

2. An analyzer according to claim 1 in which said recorder comprises a strip-chart recorder having a maximum recording rate of less than 100 mm/sec and in which said translator includes means to present the data to said recorder at a rate corresponding to an effective recording rate substantially in excess of the maximum recording rate of said recorder.

3. An analyzer according to claim 2 in which said controlling means includes means providing a data read-out rate from the translator in excess of ten times the data read-in rate thereto.

4. An analyzer according to claim 3 in which said controlling means includes means providing a data read-out rate from the translator in excess of twenty times the data read-in rate thereto.

5. An analyzer acording to claim 1 in which said data translator includes means for forming an intermediate record of the breath sound intensity means read by said transducer, said record-forming means being actuable to reproduce the data stored therein at a subsequent time for time base translation by said translator.

6. An analyzer according to claim 1 in which said transducer comprises a stethoscope for placement on a human body and providing as output an electrical signal which reproduces the sounds impinging on said stethoscope.

* * * * *